(12) United States Patent
Lagerwall et al.

(10) Patent No.: US 6,313,337 B1
(45) Date of Patent: Nov. 6, 2001

(54) METHOD OF MAKING BENZOYL HALIDES AND NITRILES

(75) Inventors: Dean R. Lagerwall, Amherst; Daniel R. Thielen, Synder; Pravin M. Khandare, Amherst; Mark F. Lechner, Sanborn, all of NY (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

(21) Appl. No.: 09/550,456

(22) Filed: Apr. 17, 2000

(51) Int. Cl.[7] .......................... C07C 17/14; C07C 22/04; C07C 253/24; C07C 255/50
(52) U.S. Cl. .................. 558/329; 558/425; 562/474; 562/861; 570/185; 570/203
(58) Field of Search .................... 558/329, 425; 570/185, 203; 562/474, 861

(56) References Cited

U.S. PATENT DOCUMENTS 5,866,709    2/1999   Hausladen .................. 558/329

OTHER PUBLICATIONS

B. F. Filimonov et al., Zh. Obshch. Khim. (1977), 47(7), 1670, titled "Chlorination of Aromatic Aldehydes by Benzotrichloride in the Presence of Iron(III) Chloride".

B. F. Filimonov et al., Zh. Obshch. Khim. (1979), 49(5), 1098–1105, titled "Oxygen–Chlorine Carbenoid Exchange Between Aldehydes and Compounds Containing a Trichloromethyl Group".

B. F. Filimonov et al., Zh. Obshch. Khim. (1980), 50(6), 1366–372, titled "Oxygen–Chloride Carbenoid Exchange Reaction Between Aldehydes and Compounds With a Trichloromethyl Group".

G. F. Dvorko et al., in Zh. Obshch. Khim. (1981), 51(9), 2067–2075, titled "Catalysis by acids and their Anhydrides of Oxygen–Chlorine Exchange Reactions Between Aryldichloromethanes and Aromatic Aldehydes".

Primary Examiner—T. A. Solola
(74) Attorney, Agent, or Firm—Richard D. Fuerle; Anne E. Brookes

(57) ABSTRACT

A method of making a benzoyl halide is disclosed. Into a reactor is placed a reaction mixture of a benzotrihalide and a benzaldehyde having the respective general formulas

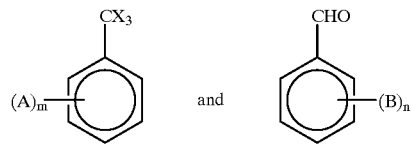

where each A is independently selected from halogen, $CF_3$, R, or OR, each B is independently selected from halogen, $CF_3$, or R, R is alkyl from $C_1$ to $C_{10}$ or aryl from $C_6$ to $C_{12}$, each X is independently selected from Cl and Br, m is 0 to 3, and n is 0 to 2. Also added is at least about 10 ppm of a catalyst selected from the group consisting of zinc salts and copper salts, and an optional solvent. The addition of an ammonium halide to the product mixture forms the corresponding amide, which can be dehydrated to form the corresponding nitrile.

20 Claims, No Drawings

METHOD OF MAKING BENZOYL HALIDES AND NITRILES

BACKGROUND OF THE INVENTION

This invention relates to a method of making a mixture of a benzoyl halide and a benzal halide by reacting a benzotrihalide with a benzaldehyde. In particular, it relates to the use of a salt of zinc or copper, such as zinc acetate, to catalyze that reaction.

Typically, water is used to partially hydrolyze benzotrihalides and produce the corresponding benzoyl halide. Due in part to the reactivity of the product with water and the co-production of 2 equivalents of HCl, this process presents a number of processing difficulties, such as overhydrolysis, which results in the formation of the corresponding benzoic acid and the reaction of the benzoic acid with the product benzoyl halide to produce benzoic anhydride. Because the benzoic acid and anhydride have a low solubility, solids can form in the reaction mixture. The HCl generated reduces the efficiency of the still during the distillation of the product. Water and benzoyl halide can be carried into the reactor vent with the HCl by entrainment and can cause plugging by forming a benzoic acid.

These processing issues can be mitigated by reacting the benzotrihalide with a benzaldehyde rather than with water. That reaction can proceed in reasonably high yield when a strong Lewis acid, such as ferric chloride, is used. However, significant tar formation has been reported. The higher distillation temperatures required to isolate the product further increases tar formation and often significantly reduces any benefits gained over the water hydrolysis method. See "Oxygen-Chlorine Carbenoid Exchange Reaction Between Aromatic Aldehydes and Compounds Containing a Dichloromethyl Group," by B. F. Filimonov et al. in Zh. Obshch. Khim. (1980), 50(6), 1366–72 (zinc chloride was tried as a catalyst in the reaction of benzaldehyde with o-chloro benzal chloride, but the yield was low.); "Oxygen-Chlorine Carbenoid Exchange Between Aldehydes and Compounds Containing a Trichloromethyl Group," by B. F. Filimonov et al. in Zh. Obshch. Khim. (1979), 49(5), 1098–105; "Chlorination of Aromatic Aldehydes by Benzotrichloride in the Presence of Iron(III) Chloride," by B. F. Filimonov et al., Zh. Obshch. Khim. (1977), 47(7), 1670; "Kinetics and Mechanism of the Chlorination of Aromatic Aldehydes with Benzotrichloride," by G. F. Dvorko et al., Zh. Obshch. Khim. (1985), 55(8), 1828–35; and "Catalysis by Acids and Their Anhydrides of Oxygen-Chlorine Exchange Reactions Between Aryldichloromethanes and Aromatic Aldehydes," by G. F. Dvorko et al., Zh. Obshch, Khim. (1981), 51(9), 2067–75.

In addition, benzonitriles can be made by reacting a benzotrihalide with an ammonium halide in the presence of a catalytic amount of a benzoic acid. An intermediate amide is formed, which is dehydrated by the benzotrihalide to form the nitrile and a benzoyl halide. The benzoyl halide reacts with additional ammonium halide to form additional amide and continue the cycle (see U.S. Pat. No. 5,866,709). To avoid introducing other compounds into the product mixture, the benzoic acid selected as the catalyst should correspond to the isomer of the benzotrihalide being reacted. Unfortunately, the corresponding benzoic acid catalyst is often difficult to obtain and/or is expensive. Additionally, benzoic acids have high melting points and present solids handling problems in the production of nitriles.

SUMMARY OF THE INVENTION

We have found that the reaction of benzotrihalides with benzaldehydes will proceed with a high yield of benzoyl halide when a salt of zinc or copper, such as zinc acetate, is used as a catalyst. Unlike the water hydrolysis process, stoichiometric amounts of hydrogen halide are not formed in this reaction and further hydrolysis of the benzoyl halide to form a benzoic acid is avoided. The high yielding process of this invention overcomes the process difficulties associated with water hydrolysis while also avoiding the tar-forming tendencies of strong Lewis acids. This invention can be applied to the reactions of a wide variety of aldehydes and benzotrihalides to generate the desired benzoyl chloride. The aldehyde and the amount of aldehyde used can be chosen so that the coproducts formed are easily separated.

We have also found that a nitrile can be made using a benzoyl chloride catalyst instead of a benzoic acid catalyst. The benzoyl chloride can either be produced in situ by reacting an aldehyde with the desired benzotrihalide or it can be produced as a separate product, which can then be fed as a reagent into a benzotrihalide/ammonium halide mixture. The benzaldehyde used in this reaction can be chosen based on the ease of separating the corresponding benzal chloride from the nitrile by distillation and does not need to have the same side chain substitution as the benzotrichloride. The benzaldehyde is also more reactive than the corresponding benzoic acid and forms less hydrogen halide byproduct.

DESCRIPTION OF THE PREFERRED EMBODIMENTS

In this invention, a benzotrihalide is reacted with a benzaldehyde to produce a mixture of a benzoyl halide and a benzal halide:

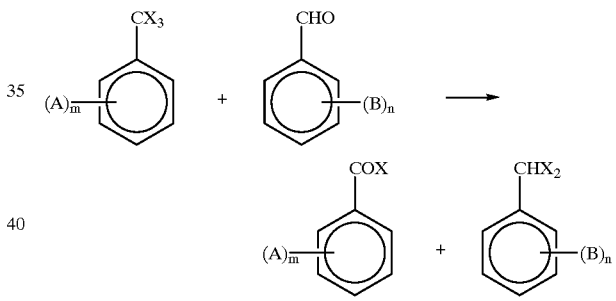

where each A is independently selected from halogen, $CF_3$, R, or OR, each B is independently selected from halogen, $CF_3$, or R, R is alkyl from $C_1$ to $C_{10}$ or aryl from $C_6$ to $C_{12}$, each X is independently selected from Cl and Br, m is 0 to 3, and n is 0 to 2. Preferably, A is Cl or $CF_3$, B is Cl, R is alkyl from $C_1$ to $C_4$, X is Cl, m is 0 to 2, and n is 0 to 1 as those compounds are of greater commercial interest. Examples of benzotrihalides that can be used include benzotrichloride (BTC), p-chlorobenzotrichloride (PCBTC), p-bromobenzotrichloride (PBBTC), 2,4-dichlorobenzotrichloride (2,4-DCBTC), 3,4-dichlorobenzotrichloride (3,4-DCBTC), and m-trifluoromethylbenzotrichloride (MTFMBTC). Examples of benzaldehydes that can be used include benzaldehyde (BAL), o-chlorobenzaldehyde (OCBAL), p-chlorobenzaldehyde (PCBAL), and p-bromobenzaldehyde (PBBAL).

While the benzotrihalide and the benzaldehyde react equimolarly, it is preferable to use a slight excess of whichever one has a boiling point that differs the most from the boiling points of the two products (typically, this is the benzotrihalide). In this way, the reactant that has the boiling point that is closest to the boiling point of one of the products can be completely reacted and it is not necessary to separate it from the product mixture. An excess of about 2 to about 40 wt % (based on total weight of the reactants) is preferred. The following table gives some examples of options that can be used to select easily-separated products:

| | Boiling Point of Isomer (° C.) | | | |
|---|---|---|---|---|
| Substitution | Benzo-trichloride | Benz-aldehyde | Benzoyl-chloride | Benzal-chloride |
| none | 219–223 | 178–179 | 198 | 205 |
| p-chloro | 254 | 217 | 228 | 239 |
| o-chloro | 264 | 213–214 | 238 | 227–228 |
| 2,4-dichloro | 288 | | 256 | |
| 3,4-dichloro | 283 | | 257 | |
| m-trifluoromethyl | 210 | | 184 | |

The reaction is catalyzed by a zinc or copper salt like $Zn(OAc)_2$, $ZnCl_2$, $Cu(OAc)_2$, or $CuCl_2$, where "OAc" is acetate. Strong Lewis acid catalysts, such as ferric chloride, do not work well in this reaction as they tend to decompose the reactants and the products, resulting in the formation of tar. Other catalysts, such as nickel chloride and nickel acetate, also do not work well. Zinc salts are preferred since they have been found to give rapid reactions in high yield. The catalyst can be added to the reaction mixture or it may be formed in situ. At least about 10 ppm catalyst (calculated as zinc chloride and based on the total amount of reactants) should be used because the reaction is too slow if less catalyst is used. Too much catalyst is unnecessary, but not harmful; a preferred amount of catalyst is about 50 to about 500 ppm.

The reaction begins slowly and then accelerates as the level of acid halide increases. The reaction can be accelerated initially by the addition of a small amount of an acid halide to the reaction mixture, preferably the same benzoyl halide that is the product of the reaction. When $Zn(OAc)_2$ is used, its conversion to $ZnCl_2$ and acetyl chloride by the benzotrihalide is particularly useful. Alternatively, after the first reaction is run, the acid halide can be a small amount of the benzoyl halide product left in the reactor or recycled from product distillation. The amount of acid halide used for this purpose is preferably 0.1 to 25 wt % based on the benzotrichloride charged. Less than 0.1 wt % may not significantly increase the initial reaction rate and more than 25 wt % will significantly reduce reactor throughput. The speed of the reaction and the reaction temperature can be controlled by the rate at which the benzaldehyde is added to the mixture of the benzotrihalide and the catalyst.

A solvent is not required for the reaction, but can be used to aid in the transport of reactants or to remove excess heat. For example, a solvent such as p-chlorobenzotrifluoride, which boils at about 160° C., can be added and refluxed to maintain the reaction temperature at 160° C. About 5 to about 50 wt % of the solvent (based on the weight of the reactants) is preferred as less exerts little temperature control and more reduces the reactor throughput.

The products can be separated by distillation. The benzoyl chloride products are useful as agricultural or pharmaceutical intermediates. The benzal chloride product can be recycled to regenerate the benzaldehyde by hydrolysis or it can be sold. The hydrolysis of the benzal chloride to the aldehyde occurs without forming the acid or the anhydride and presents fewer processing problems than the direct water hydrolysis of benzotrihalides.

A nitrile can be formed from the in situ generated or isolated benzoyl halide product by reaction with ammonia or an ammonium halide, first forming an intermediate amide:

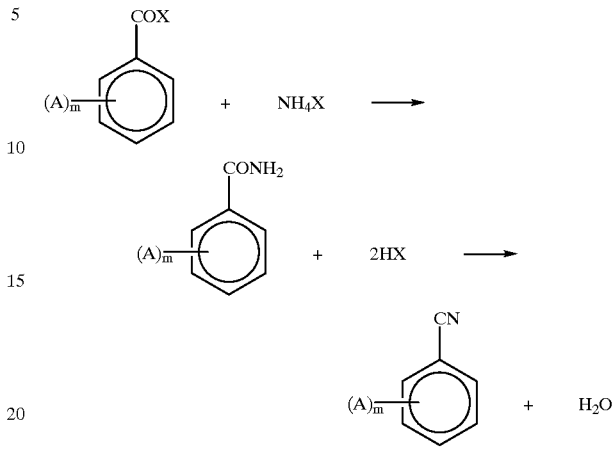

Zinc salts do not interfere with the nitrilation process while $FeCl_3$ causes low yield due to trimer formation (triazine). Particularly useful is the in situ generation of a catalytic amount of the benzoyl halide used to initiate the nitrilation process by reacting a benzaldehyde with the benzotrihalide. The benzaldehyde used in that reaction need not be the benzaldehyde having the same aromatic substitution as the desired benzotrihalide reactant, but can be chosen for its availability and the ease with which the resulting benzal halide can be separated. The preferred amount of aldehyde is between 0.02 and 0.15 equivalents based on the benzotrihalide. An ammonium halide (or $NH_3$) is added to the benzoyl halide/benzotrihalide mixture at about 150 to about 220° C. The ammonium halide can be ammonium chloride, ammonium bromide, or ammonium fluoride, but ammonium chloride is preferred as it is inexpensive. The dehydration of the amide to form the nitrile results by reaction with either the benzotrihalide or the benzoyl halide and occurs at about 150 to about 250° C.

The following examples further illustrate this invention:

EXAMPLE 1

PCBTC (1306.1 g) and $Zn(OAc)_2$ (0.41 g) were heated to 140° C. PCBAL (773 g) was added over 75 minutes. After stirring for 2 hours, no PCBAL was observed by GC. The major reaction products were p-chloro benzoyl chloride (PCBOC), p-chlorobenzal chloride (PCBAC), and unreacted PCBTC. Distillation gave an 87% yield of 99.72% pure PCBOC.

EXAMPLE 2

2,4-DCBTC (200.6 g, 0.76 mole) and $Zn(OAc)_2$ (0.09 g) were heated to 170° C. OCBAL (96.0 g, 0.68 mole) was added over 35 minutes. After stirring for 2 hours, less than 1 mole % OCBAL remained. Analysis by gas chromatography (GC) showed 0.35% OCBAL, 44.5% o-chloro benzal chloride (OCBAC), 45.5% 2,4-dichlorobenzoyl chloride (2,4-DCBOC), and 6.7% 2,4-DCBTC. The mixture was readily separable by distillation to produce pure 2,4-DCBOC.

EXAMPLE 3

2,4-DCBTC (200.5 g, 0.76 mole) and $Zn(OAc)_2$ (0.09 g) were heated to 170° C. OCBAL (100.3 g, 0.74 mole) was added over 65 minutes. After stirring for 2 hours, less than 1 mole % OCBAL remained. GC analysis showed 0.3% OCBAL, 44.9% OCBAC, 43.0% 2,4-DCBOC and 5.4% 2,4-DCBTC. The mixture was readily separable by distillation to produce pure 2,4-DCBOC.

EXAMPLE 4 - COMPARATIVE

Other catalysts are unsatisfactory in this reaction for the reasons given in the following table:

| Catalyst | Results/Comments |
|---|---|
| Nickel chloride | No reaction |
| Ferric chloride | High tar formation |
| Mercury chloride | Not industrially useful |

We claim:
1. A method of making a mixture of a benzoyl halide and a benzal halide comprising
    (A) in a reactor forming a reaction mixture of
        (1) a benzotrihalide having the general formula

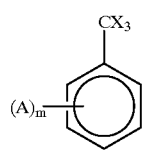

where each A is independently selected from halogen, $CF_3$, R, or OR, each X is independently selected from Cl and Br, and m is 0 to 3;
        (2) a benzaldehyde having the general formula

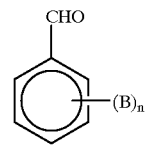

where each B is independently selected from halogen $CF_3$, or R, R is alkyl from $C_1$ to $C_{10}$ or aryl from $C_6$ to $C_{12}$, and n is 0 to 2;
        (3) at least about 10 ppm of a catalyst selected from the group consisting of zinc salts and copper salts; and
        (4) an optional solvent, whereby said benzotrihalide reacts with said benzaldehyde to form said benzoyl halide and said benzal halide; and
    (B) separating said benzoyl halide.
2. A method according to claim 1 wherein said benzotrihalide is p-chlorobenzotrichloride.
3. A method according to claim 1 wherein said benzotrihalide is 2,4-dichlorobenzotrichloride.
4. A method according to claim 1 wherein said benzotrihalide is 3,4-dichlorobenzotrichloride.
5. A method according to claim 1 wherein said benzotrihalide is m-trifluoromethylbenzotrichloride.
6. A method according to claim 1 wherein said benzaldehyde is o-chlorobenzaldehyde.
7. A method according to claim 1 wherein said benzaldehyde is p-chlorobenzaldehyde.
8. A method according to claim 1 wherein said catalyst is a zinc salt.
9. A method according to claim 8 wherein zinc salt is zinc acetate, which is formed in situ.
10. A method according to claim 1 including the additional last step of adding ammonia or an ammonium halide to the product mixture to react with said benzoyl halide and form the corresponding amide, then dehydrating said amide to form the corresponding nitrile.
11. A method according to claim 1 wherein there is about 2 to about 40 wt % excess of the benzotrihalide reactant.
12. A method according to claim 1 wherein about 5 to about 50 wt % of a solvent is included in said reaction mixture.
13. A method according to claim 1 wherein said benzaldehyde is added to a mixture of said benzotrihalide and said catalyst.
14. A method according to claim 1 wherein about 1 to about 25 wt % of an acid halide is initially added to said reaction mixture.
15. A method according to claim 14 wherein said acid halide is the same as the benzyl halide product of said reaction.
16. A method of making a benzoyl chloride comprising
    (A) in a reactor forming a reaction mixture which comprises
        (1) a benzotrichloride having the general formula

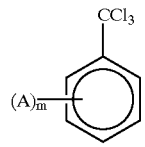

where each A is independently selected from chlorine and $CF_3$ and m is 0 to 2;
        (2) a monochlorobenzaldehyde;
        (3) about 50 ppm to about 500 ppm of a zinc salt; and
        (4) an optional solvent, whereby said benzotrichloride reacts with said monochlorobenzaldehyde to form a benzoyl chloride and a benzal chloride; and
    (B) isolating said benzoyl chloride product by distillation.
17. A method according to claim 16 wherein said zinc salt is zinc acetate.
18. A method according to claim 16 including the additional last steps of adding ammonium chloride to the product mixture to react with said benzoyl chloride and form the corresponding amide, then dehydrating said amide to form the corresponding nitrile.
19. A method of making a benzoyl chloride comprising
    (A) in a reactor forming a reaction mixture of
        (1) a benzotrichloride selected from the group consisting of p-chlorobenzotrichloride, 2,4-dichlorobenzotrichloride, and 3,4-dichlorobenzotrichloride;
        (2) about 50 ppm to about 500 ppm of a catalyst selected from the group consisting of zinc chloride, zinc acetate, and mixtures thereof; and
        (3) about 1 to about 25 wt % of the corresponding benzoyl chloride product; and
    (B) slowly adding to said reaction mixture a benzaldehyde selected from the group consisting of o-chlorobenzaldehyde and p-chlorobenzaldehyde, whereby said benzotrichloride reacts with said benzaldehyde to form a benzoyl chloride and a benzal chloride; and
    (C) isolating the benzoyl chloride product by distillation.
20. A method according to claim 19 including the additional last steps of adding ammonium chloride to the product mixture to react with said benzoyl chloride and form the corresponding amide, then dehydrating said amide to form the corresponding nitrile.

* * * * *